(12) United States Patent
Fujii et al.

(10) Patent No.: US 8,285,003 B2
(45) Date of Patent: Oct. 9, 2012

(54) PERSONAL AUTHENTICATION METHOD AND PERSONAL AUTHENTICATION DEVICE UTILIZING OCULAR FUNDUS BLOOD FLOW MEASUREMENT BY LASER LIGHT

(75) Inventors: Hitoshi Fujii, Munakata (JP); Naoki Konishi, Iizuka (JP)

(73) Assignees: Kyushu Institute of Technology, Fukuoka (JP); Syscom Japan, Inc., Fukuoka (JP)

(*) Notice: Subject to any disclaimer, the term of this patent is extended or adjusted under 35 U.S.C. 154(b) by 894 days.

(21) Appl. No.: 12/303,461

(22) PCT Filed: May 28, 2007

(86) PCT No.: PCT/JP2007/060776
§ 371 (c)(1),
(2), (4) Date: Dec. 4, 2008

(87) PCT Pub. No.: WO2007/142055
PCT Pub. Date: Dec. 13, 2007

(65) Prior Publication Data
US 2009/0202113 A1 Aug. 13, 2009

(30) Foreign Application Priority Data
Jun. 7, 2006 (JP) .................. 2006-158542

(51) Int. Cl.
*G06K 9/00* (2006.01)
*A61B 5/00* (2006.01)
*A61B 5/02* (2006.01)
(52) U.S. Cl. ......... 382/117; 382/128; 600/310; 600/504

(58) Field of Classification Search .................. 382/117, 382/128, 321; 356/71, 39; 600/476, 473, 600/504, 489, 320, 407, 475, 431, 322, 323, 600/318, 317, 310, 479; 385/123; 351/206, 351/221, 205, 213, 215, 246, 200, 210, 211, 351/219
See application file for complete search history.

(56) References Cited

U.S. PATENT DOCUMENTS
7,817,256 B2 * 10/2010 Fujii et al. .................. 356/71

FOREIGN PATENT DOCUMENTS
JP 04-242628 A 8/1992
(Continued)

*Primary Examiner* — Sheela Chawan
(74) *Attorney, Agent, or Firm* — Sughrue Mion, PLLC (57) ABSTRACT

A personal authentication method comprising imaging, on an image sensor as a laser speckle using an optical system, light reflected from retinal blood vessels of the ocular fundus and a blood vessel layer in ocular fundus internal tissue when a laser beam is expanded and made to irradiate the ocular fundus, calculating a quantity that represents the rate of change with respect to time of the amount of light received for each pixel of the laser speckle, obtaining an ocular fundus blood flow map as a two-dimensional map of the numerical values of the quantity, and comparison-checking against pre-registered personal data utilizing at least one, observed in the blood flow map, of blood flow distribution data, a pattern reflecting the course of retinal blood vessels, a pattern reflecting the course of blood vessels in ocular fundus internal tissue observed superimposed thereon, and data on changes thereof over time, and a device therefor. In accordance with the method and device of the present invention utilizing the ocular fundus blood flow rate map, a personal authentication method and device can be obtained that have remarkably higher accuracy than conventional methods and devices.

15 Claims, 5 Drawing Sheets

FOREIGN PATENT DOCUMENTS

| | | |
|---|---|---|
| JP | 05-073666 A | 3/1993 |
| JP | 05-028133 B2 | 4/1993 |
| JP | 05-028134 B2 | 4/1993 |
| JP | 08-016752 A | 1/1996 |
| JP | 08-112262 A | 5/1996 |
| JP | 10-005196 A | 1/1998 |
| JP | 11-149453 A | 6/1999 |
| JP | 11-215119 A | 8/1999 |
| JP | 2003-164431 A | 6/2003 |
| JP | 2003-180641 A | 7/2003 |
| JP | 2003-331268 A | 11/2003 |
| JP | 2006-107028 A | 4/2006 |
| WO | 2005/122896 A1 | 12/2005 |
| WO | 2006/046627 A1 | 5/2006 |

* cited by examiner

PERSONAL AUTHENTICATION METHOD AND PERSONAL AUTHENTICATION DEVICE UTILIZING OCULAR FUNDUS BLOOD FLOW MEASUREMENT BY LASER LIGHT

TECHNICAL FIELD

The present invention relates to a personal authentication method and a personal authentication device utilizing ocular fundus blood flow measurement and, more particularly, to a personal authentication method and device in which blood flow in blood vessels of internal tissue such as the retina or the choroid is measured using a specific laser beam.

BACKGROUND ART

With regard to personal authentication, a method using a fingerprint has been widespread for a long time, but recently, as a replacement for visual comparison, various automatic authentication methods in which an image sensor or a semiconductor sensor is combined with image processing by a computer have been developed and widely utilized. Furthermore, recently, a method for personal authentication by reading a subcutaneous vein pattern of a fingertip or the palm of a hand by means of near-infrared light and an image sensor and extracting characteristics such as branching points has been put into practice. However, none of these methods is yet perfect, and the fight against forgery is continuing.

For example, Patent Publications 1 and 2 disclose a clear high-resolution fingerprint sensor using laser light, but this cannot discriminate a forged fingerprint. In contrast thereto, Patent Publication 3 discloses a method in which personal authentication is carried out by a vein pattern using a normal light beam and, furthermore, it is determined whether or not a subject that is authenticated is living by optical detection of the pulse. Although this is not authentication of a fingerprint, it is effective in preventing forgery since it can be confirmed whether the subject that is authenticated is living. However, there are problems with the reliability of authentication by a vein pattern, the complexity of equipment, etc.

(Patent Publication 1) JP-A-5-73666 (JP-A denotes a Japanese unexamined patent application publication)
(Patent Publication 2) JP-A-8-16752
(Patent Publication 3) JP-A-2003-331268

On the other hand, it is known that, when laser light is shone on a living body, the intensity distribution of reflected scattered light thereof forms a dynamic laser speckle (random spot pattern) due to moving scattering particles such as blood cells; this pattern is detected on an imaging plane by an image sensor, and by quantifying changes over time of the pattern in each pixel and displaying them as a map, it is possible to image the blood flow distribution of capillary vessels in the vicinity of the surface of the living body. Using such a phenomenon, techniques and devices for measuring a blood flow map of the area underneath the skin or of the ocular fundus have been proposed by the present inventors (ref. e.g. Patent Publications 4 to 9).

(Patent Publication 4) JP-B-5-28133 (JP-B denotes a Japanese examined patent application publication)
(Patent Publication 5) JP-B-5-28134
(Patent Publication 6) JP-A-4-242628
(Patent Publication 7) JP-A-8-112262
(Patent Publication 8) JP-A-2003-164431
(Patent Publication 9) JP-A-2003-180641

The present inventors have carried out an intensive investigation into the concept of combining a blood flow map and a fingerprint pattern for use in personal authentication, and have already proposed a personal authentication method involving measuring subcutaneous blood flow and means therefor. That is, there have been proposed a personal authentication method comprising (1) a step of imaging, on an image sensor as a laser speckle using an optical system, light reflected from a subcutaneous blood vessel layer when a laser beam is expanded and made to irradiate a finger pad, (2) a step of determining a quantity that represents the rate of a change with respect to time of the amount of light received for each pixel of the laser speckle, for example, the average rate of change with respect to time, or the reciprocal of the magnitude of the variation in the amount of light received integrated over the exposure time of the image sensor, and obtaining a finger pad blood flow map as a two-dimensional map of numerical values thereof, and (3) a step of comparing and evaluating a fingerprint pattern represented as a blood flow map against pre-registered personal data, and devices for carrying out each step (Patent Publication 10).

(Patent Publication 10) International Patent Application WO2005/122896

Furthermore, the present inventors have improved the above-mentioned methods, and have invented a method and means in which a fingertip is irradiated with one laser beam at a specific wavelength as irradiation light, or with a plurality of laser beams at different wavelengths at the same time or in sequence to give a superimposed blood flow rate map or a plurality of blood flow rate maps with respect to reflected light (PCT/JP2007/050060). The depth of penetration of a laser into tissue depends on the wavelength of the laser; with light having a short wavelength such as visible light, only a blood flow distribution close to the surface, that is, a fingerprint pattern, is obtained, but since light having a long wavelength such as near-infrared light enters deep into the tissue, a blood flow map reflecting a blood flow distribution in the interior can be obtained. There is a difference in blood flow distribution in the interior between individuals, and since it is difficult to forge, if this is added to authentication data the accuracy of personal verification is improved due to a synergistic effect.

Conventionally, a method and a device for forming signature data or a password by coding and encrypting personal biological information, for example, information from a photographic image of the ocular fundus, have been proposed (ref. Patent Publications 11 to 12).

However, no proposal has been made so far for a combination of blood flow data such as the course of blood vessels on the retina and the distribution profile of arteries and veins and, furthermore, distribution in a choroid blood vessel layer present behind the retina and a change in blood flow over time obtained by imaging of ocular fundus blood flow with the personal authentication method previously proposed by the present inventors.

(Patent Publication 11) JP-A-11-215119
(Patent Publication 12) JP-A-11-149453

DISCLOSURE OF INVENTION

Problems to be Solved by the Invention

The present inventors have examined ocular fundus blood flow rate distribution by using a method and a device for determining an ocular fundus blood flow rate map by irradiating the ocular fundus with an expanded laser beam, imaging the irradiated spot on a two-dimensional image sensor using an optical system, and measuring the change over time in an interference pattern generated on the image plane per pixel, and it has been found that all blood flow data such as the course of blood vessels on the retina and the distribution profile of arteries and veins and, furthermore, distribution in the choroid blood vessel layer present behind the retina and the change in blood flow over time can be utilized for personal authentication. It is therefore an object of the present invention to provide, based on the above-mentioned findings, a personal authentication method and device that have remarkably high accuracy compared with conventional methods and devices by utilizing an ocular fundus blood flow rate map obtained by irradiating the ocular fundus with a laser beam.

Means for Solving the Problems

Among the present inventions, the invention described in Claim 1 is a personal authentication method comprising imaging, on an image sensor as a laser speckle using an optical system, light reflected from retinal blood vessels of the ocular fundus and a blood vessel layer in ocular fundus internal tissue when a laser beam is expanded and made to irradiate the ocular fundus, calculating a quantity that represents the rate of change with respect to time of the amount of light received for each pixel of the laser speckle, obtaining an ocular fundus blood flow map as a two-dimensional map of numerical values of the quantity, and comparison-checking the blood flow map against pre-registered personal data, wherein the blood flow map obtained from reflected light is measured using a laser beam that can reach the internal tissue of the ocular fundus, and comparison-checking against pre-registered personal data is carried out utilizing at least one, observed in the blood flow map, of blood flow distribution data, a pattern reflecting the course of retinal blood vessels, a pattern reflecting the course of blood vessels in ocular fundus internal tissue observed superimposed thereon, and data on changes thereof over time.

The invention described in Claim 2 is the personal authentication method according to Claim 1, wherein as the laser beam one or a plurality of laser beams in the range of visible light to near-infrared light is used.

The invention described in Claim 3 is the personal authentication method according to Claim 1 or 2, wherein the laser light is near-infrared laser light having a wavelength in the range of about 770 to 1500 nm.

The invention described in Claim 4 is the personal authentication method according to any one of Claims 1 to 3, wherein a camera section that can observe the position of the laser beam when passing through the pupil is provided separately, and positioning of the optical system is controlled by processing an image signal obtained from the camera section. When accurately irradiating a measurement area of the ocular fundus with a laser, it is necessary to prevent the laser beam passing through the pupil surface from being vignetted by the pupil, and by providing the camera section for observing the pupil surface and controlling a drive mechanism for the overall blood flow measurement system by processing an image signal obtained from the camera section it is possible to carry out adjustment so that a laser beam passes through an appropriate position within the pupil aperture.

The invention described in Claim 5 is the personal authentication method according to any one of Claims 1 to 4, wherein in order to observe the course of blood vessels in the optic papilla region the line of sight is guided. In this invention, in order to observe the blood vessel pattern of the optic papilla region, which is where retinal blood vessels are concentrated, the line of sight is guided.

The invention described in Claim 6 is a personal authentication device comprising one or a plurality of irradiating means that expand a near-infrared laser beam and irradiate the ocular fundus, light-receiving means that has a large number of pixels and receives light reflected from retinal blood vessels of the ocular fundus and a blood vessel layer in ocular fundus internal tissue, storage means that stores the output of each of the pixels obtained by the light-receiving means, calculating means that calculates a quantity representing the rate of change with respect to time of the amount of light received for each pixel using stored contents of the storage means, second storage means that stores a two-dimensional distribution of the calculation results obtained for each of the pixels as a blood flow map, means for extracting at least one, observed in the blood flow map stored by the second storage means, of blood flow distribution data, a pattern reflecting the course of retinal blood vessels, a pattern, observed superimposed thereon, reflecting the course of blood vessels in ocular fundus internal tissue, and information on changes thereof over time, and means for comparing and judging the extracted data against pre-registered personal data.

The invention described in Claim 7 is the personal authentication device according to Claim 6, wherein a camera section that can observe the position of the laser beam when passing through the pupil is provided separately, and the device comprises means for controlling the positioning of the optical system by processing an image signal obtained from the camera section.

Furthermore, the invention described in Claim 8 is the personal authentication device according to Claim 6 or 7, wherein the device comprises means for guiding the line of sight in order to observe the course of blood vessels in the optic papilla region.

Effects of the Invention

It can be said that the personal authentication method of the present invention is more difficult to forge compared with a password or a PIN. All conventional arrangements utilize information of a part close to the surface of a living body such as unevenness of the skin, veins under the skin, or a blood flow distribution, and it cannot be denied that there is therefore a possibility of a third party stealing biometric information by placing a sensor without the subject noticing. The present invention is similar to a personal authentication method involving measurement of blood flow in a finger pad proposed previously by the present inventors in terms of application of the technique of imaging blood flow by utilizing a laser speckle, but it is characterized in that ocular fundus blood flow, which is present in a deeper region and cannot easily be comprehended, is selected as a measurement target.

When carrying out personal authentication, although it is generally difficult to generate a blood flow distribution mimicking a retinal blood vessel pattern for the purpose of imitation, it is even more difficult to superimpose it on a blood flow distribution of ocular fundus internal tissue or a pulse component. The method of the present invention can therefore build a more secure authentication system than the personal authentication method and means employing finger pad blood flow.

BRIEF DESCRIPTION OF DRAWINGS (FIG. 1) A diagram for explaining a personal authentication method employing measurement of ocular fundus blood flow.

EXPLANATION OF REFERENCE NUMERALS AND SYMBOLS

1 Eyeball
2 Pupil
3 Laser beam spot
4 Laser spot on ocular fundus as target location for imaging blood flow
5 Semiconductor laser
6 Mirror
7 Lens
8 Objective lens
9, 10 Light-emitting diode guiding line of sight
11 Dichroic mirror
12 Optical system
13, 14 Image sensor
15 Sensor section
16 Optic papilla region
17 Artery and vein
18 Blood vessel within internal tissue

BEST MODE FOR CARRYING OUT THE INVENTION

Among biometric information, information obtained from blood flow has the characteristic that authentication cannot be carried out unless a sensor is operated in a state in which a subject is alive. The present invention measures a blood flow distribution, etc. of blood vessels on the retina or blood vessels of ocular fundus internal tissue by a blood flow measurement technique employing laser scattering in which a laser beam is first expanded and made to irradiate the ocular fundus, and light reflected from retinal blood vessels and a blood vessel layer present in ocular fundus internal tissue such as the choroid is imaged as a laser speckle on an image sensor using an optical system. The laser speckle is scanned continuously using an image sensor, a quantity representing the rate of change with respect to time of the amount of light received for each pixel, for example, the average change over time, or the reciprocal of the magnitude of the variation in the amount of light received integrated over the exposure time of the image sensor is calculated, and the numerical values thus obtained are converted into a two-dimensional map, thus giving a blood flow map of the ocular fundus. By comparison-checking various data observed in this blood flow map against pre-registered personal data, personal authentication becomes possible.

One of the methods of the present invention is a personal authentication method wherein a laser beam having a long wavelength, which can reach the internal tissue of the ocular fundus, and preferably a near-infrared laser beam, is used to measure an ocular fundus blood flow map obtained from light reflected therefrom, and comparison-checking against pre-registered personal data is carried out. Another method is a method wherein a plurality of laser beams in the range of visible light to near-infrared light, and preferably a near-infrared laser beam and a laser beam having a shorter wavelength than this, preferably a visible laser beam, are used in combination, ocular fundus blood flow maps obtained from the respective reflected lights are measured at the same time or in sequence, and the two types of blood flow maps thus superimposingly obtained are comparison-checked against pre-registered personal data.

In measurement of ocular fundus blood flow in this invention, for example, when laser light having a wavelength around 830 nm is used, a blood flow distribution image (blood flow map) of blood vessels present on the surface of the ocular fundus such as retinal blood vessels is obtained superimposed on a blood flow distribution of internal tissue such as the choroid. In this invention, at least one, observed in the blood flow map, of blood flow distribution data, a pattern reflecting the course of blood vessels in the retina, a pattern reflecting the course of blood vessels in the ocular fundus internal tissue observed overlapping the above, and data of changes thereof over time is utilized, and personal authentication is carried out by comparison-checking this against pre-registered personal data.

Laser light has a different depth of penetration into tissue depending on its wavelength; when light having a short wavelength such as visible light is used, only a blood flow distribution close to the surface is obtained, but when light having a long wavelength such as near-infrared light is used, since it penetrates deep into the tissue, a blood flow map reflecting the blood flow distribution of an inner region is obtained. Among the present inventions, another method constructs a personal authentication method having higher accuracy by combining these two phenomena. Furthermore, in the present invention, when data of a subject are registered, blood flow maps obtained by lasers with a plurality of wavelengths are registered, and employing a method in which the data are changed over at any time by the subject or the authentication system can also be useful for defending against impersonation.

As a visible laser beam, one of about 380 to 770 nm can be utilized, but one of about 600 to 700 nm is preferable, and one of about 630 to 650 nm is particularly preferable.

As a near-infrared laser beam, one of about 770 to 1500 nm is normally used, one of about 800 to 900 nm is preferable, and one having a wavelength of about 830 to 850 nm is particularly preferable when the sensitivity of the image sensor is taken into consideration.

Figure 1:
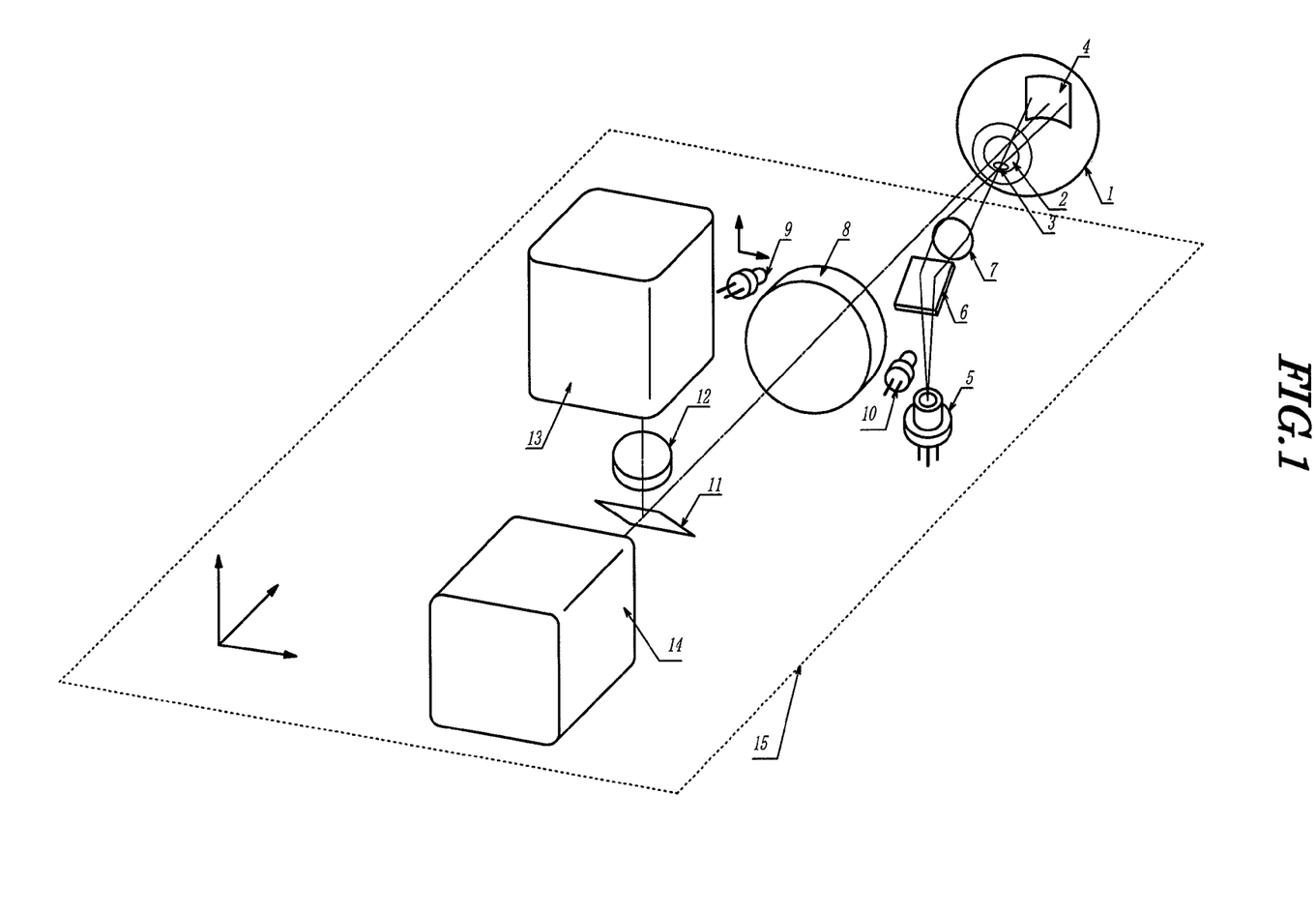

The principle of the present invention is explained in detail below by reference to drawings. FIG. 1 is a diagram for explaining a personal authentication method in which measurement of ocular fundus blood flow is utilized. 1 denotes an eyeball, 2 denotes a pupil, 3 denotes a spot of a laser beam passing through the pupil, 4 denotes a target location for imaging blood flow at a laser spot on the ocular fundus, 5 denotes a semiconductor laser, 6 denotes a mirror, 7 denotes a lens for projecting a laser on the ocular fundus, 8 denotes an objective lens for imaging the ocular fundus on an imaging system, 9 and 10 are light-emitting diodes for guiding the line of sight, 11 denotes a dichroic mirror, 12 denotes an optical system for observing the pupil and its surroundings, and 13 and 14 are image sensors such as a CCD camera. The area inside broken line 15 denotes the overall sensor section of the present invention.

Figure 2:
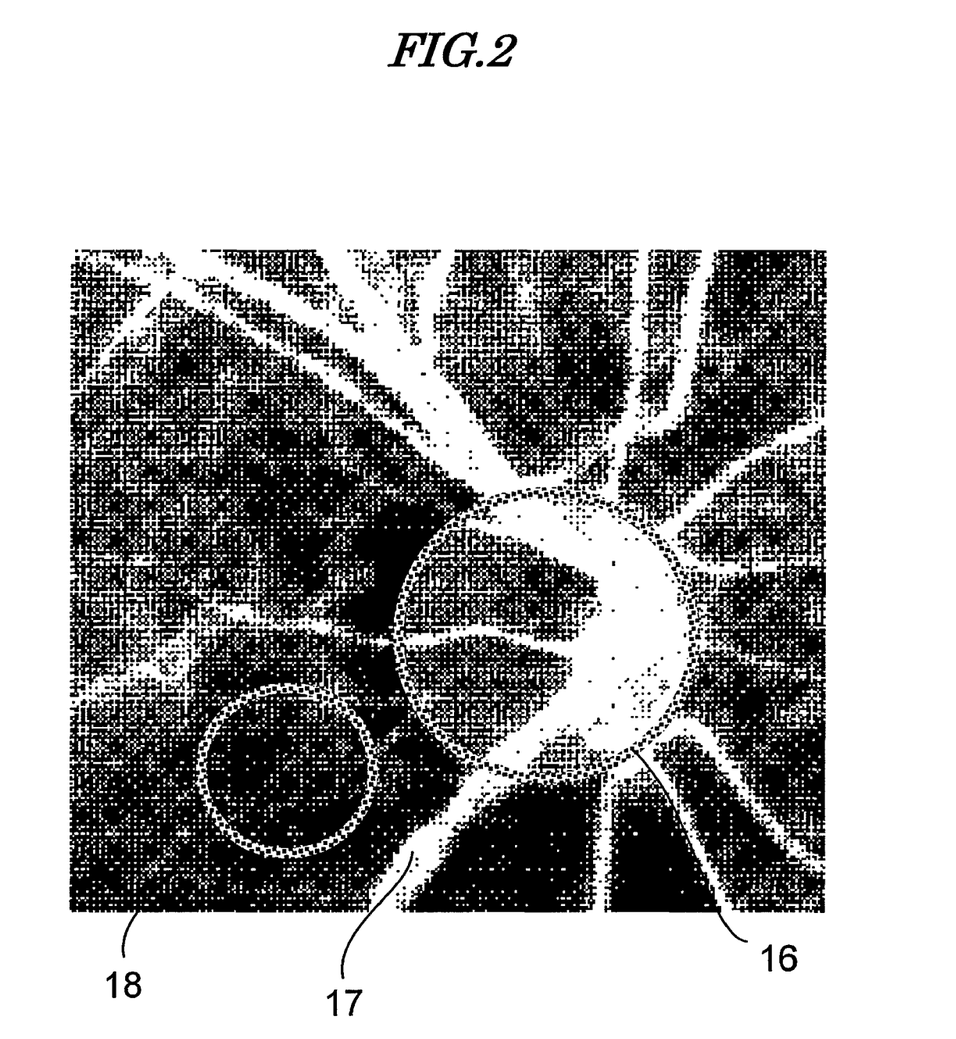
(FIG. 2) An example of measurement of an ocular fundus blood flow map.

A laser beam emitted from the semiconductor laser 5 is brought to a focus within the pupil by the lens 7, and reducing the spot size when passing through the pupil makes the beam resistant to vignetting by the pupil and enlarges the spot projected on the retina. An image of the laser spot on the ocular fundus is formed on the image sensor 14 via the objective lens 8 and the dichroic mirror 11, which allows only laser wavelength to pass through. During this process, a speckle field reflecting a blood flow rate distribution in the retina is formed on the image plane, and analyzing this by computer enables a retinal blood flow map, as shown in FIG. 2, to be extracted.

This map is one in which blood flow value data computed by a known technique and stored as a two-dimensional array in a computer are rendered so that the higher the value the whiter the dot. In FIG. 2, a blood flow map of an optic papilla region 16 and its surroundings within the ocular fundus is captured, and it is known that blood flow values and the distribution thereof in arteries and veins 17 extending out from the papilla and blood flow values and the distribution thereof in blood vessels 18 within internal tissue such as the choroid appearing faintly in areas other than the above are different depending on the individual, and unless there is an acute eye disease they do not change for a long period of time. It is therefore possible to utilize them as personal authentication data with remarkably high accuracy by reading and comparing the blood flow values of individual blood vessels, or analyzing the characteristics of the pattern of the course of blood vessels.

Figure 3:
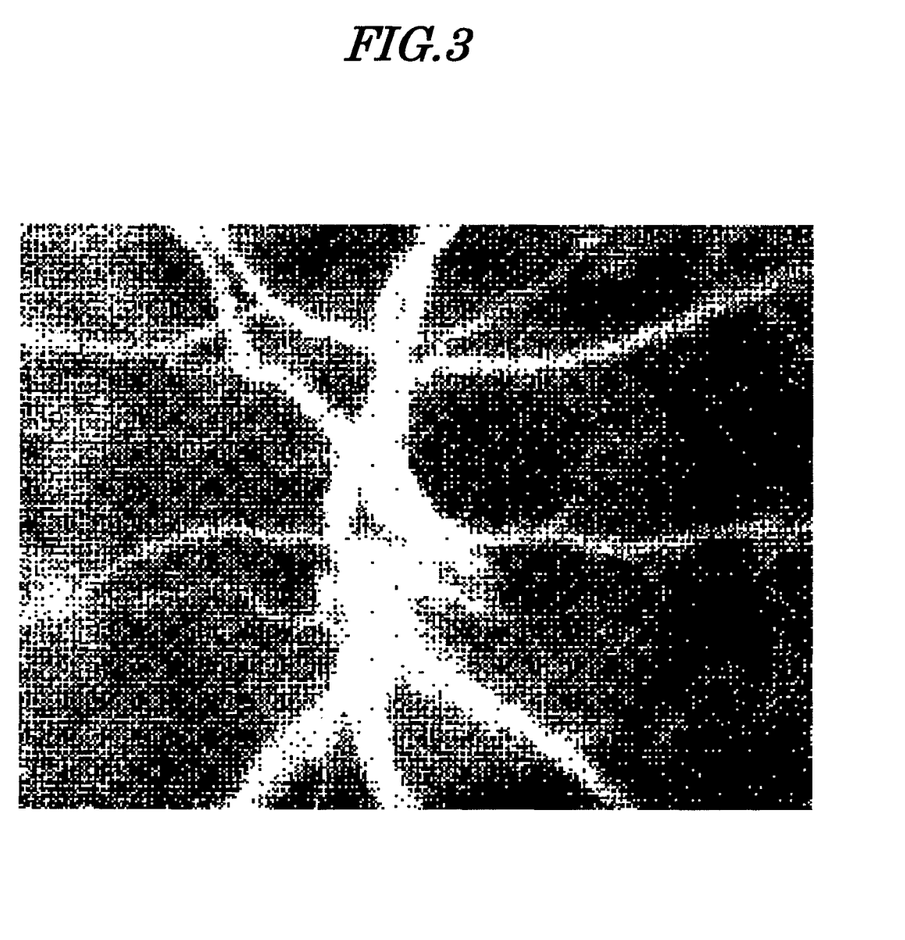
(FIG. 3) An example of measurement of an ocular fundus blood flow map (at a time of maximum blood flow).
Figure 4:
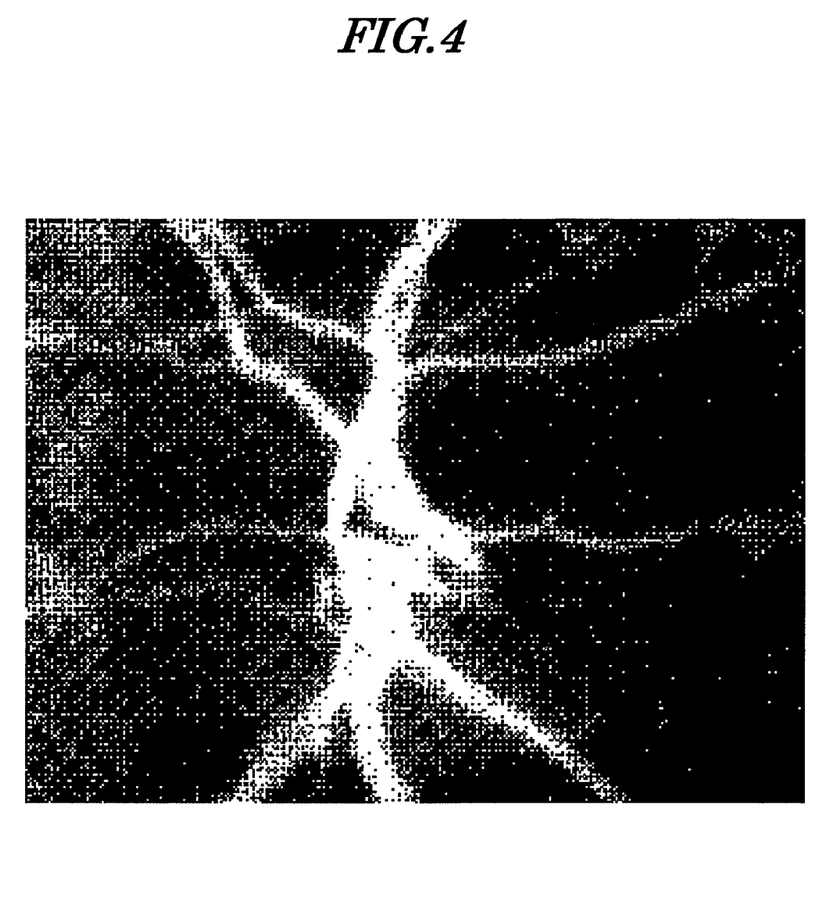
(FIG. 4) An example of measurement of an ocular fundus blood flow map (at a time of minimum blood flow).

Data utilized in conventional personal authentication are strictly concerned with pattern information; for example, in the case of a fingerprint it is the pattern formed by connections between ridge parts, and in the case of vein authentication it is the pattern formed by vein blood vessels. Numerical values handled therein concern information on whether or not a peak or a valley, or a vein is seen (that is, 1 or 0) at a given coordinate. However, in ocular fundus blood flow distribution data, not only is there pattern information on the location and branching of artery and vein blood vessels, but blood flow values (e.g. analog values from 0 to 255) at the coordinates are recorded as a two-dimensional array. Furthermore, these blood flow distribution data vary over time. For example, FIG. 3 is a blood flow map at a time of a maximum blood flow when the heart contracts, FIG. 4 is a blood flow map at a time of a minimum blood flow when the heart expands, and it can be seen that the values in each section are very different. That is, the blood flow distribution data are expressed by a function $f(x, y, t)$ having the three variables of time t and two-dimensional space $(x, y)$, and it is apparent that the distribution of values is very different among individuals. It can be seen that, compared with a conventional comparison method involving patterns alone, there is an order-of-magnitude increase in the amount of information that can be utilized, and it is extremely difficult to forge. It is of course possible to convert these analog quantities into binary form, thus reducing the calculation time, and when so doing the options are wider.

Furthermore, in the present invention, the manner in which the blood flow within these blood vessels repeatedly increases and decreases in synchronism with the heart beat can be observed, and the pattern of variation thereof is clearly different between arteries and veins. There are conventional devices in which a blood vessel pattern in the iris, etc. is utilized for personal authentication, but they merely observe the pattern of the course of blood vessels by means of an image sensor, and do not analyze the distribution of blood flow values or variation thereof. In the present invention, analyzing blood flow values in each area of the retinal blood vessels and the variation over time thereof, that is, the gradient of the rise and fall of blood flow waveform, can be utilized effectively in authentication. Moreover, if the amplitude of blood flow variation at each point on the retina is calculated and displayed on a map, this also is data unique to an individual. In this way, utilizing a retinal blood flow map enables remarkably large variety of data for personal authentication to be provided compared with conventional methods.

In the present invention, when laser light having a long wavelength is used, a map reflecting the blood flow in a deeper region is obtained. By incorporating a plurality of, preferably two, lasers from visible light to near-infrared into a device, and irradiating internal tissue such as the retina or the choroid simultaneously or separately, it is possible to extract maps having different blood flow distributions. When registering personal information in advance, by specifying the wavelength of laser light to be used for authentication, since this is known only to the subject, this can be utilized for defense against impersonation.

In the present invention, in order to accurately irradiate a measurement area of the ocular fundus with laser light, it is necessary to prevent the laser beam passing through the pupil surface from being vignetted by the pupil. By providing a camera section for observing the pupil surface, processing an image signal obtained therefrom, and controlling a drive mechanism for the overall blood flow measurement system, it is possible to make the laser beam pass through an appropriate position within the pupil aperture. For example, the method below is employed therefor.

In FIG. 1, the area inside the broken line 15 denotes the overall sensor section for ocular fundus blood flow measurement. If laser light overlaps the light path for observation of the ocular fundus when it passes through the pupil, reflection from the surface of the cornea is projected on the image sensor as a bright point, and the blood flow of that area cannot be analyzed. In order to avoid this, it is necessary to pass the laser light through the area around the pupil at a minimum spot diameter, but the position of the eyeball is not necessarily the same for each measurement (authentication). In order to solve this problem, in the present invention the optical system 11, 12 for observing the pupil and its surroundings is provided, and a mechanism is employed in which an image of the pupil 2, the laser spot 3, and the surroundings thereof is captured by the image sensor 13 and taken into a personal computer, and the overall sensor 15 is driven so that the laser spot passes through an appropriate position within the pupil.

Furthermore, in the present invention, in order to observe a blood vessel pattern of the optic papilla region where the retinal blood vessels are concentrated, it is preferable to guide the line of sight. In order to do so, for example, the method below is employed.

In FIGS. 1, 9 and 10 denote a light-emitting diode (LED) for guiding the line of sight, which is called a fixation target in an ocular fundus camera, etc. Moving this while making the subject stare at it makes the eyeball rotate and enables the location to be observed to be guided into the field of observation of the imaging system. As shown in FIG. 2, since the retinal blood vessels extend from the optic papilla to its surroundings, the course of the blood vessels is characterized by a group of blood vessels in the vicinity of the optic papilla. Furthermore, since in this location a mixture of a very high blood flow value for the interior of large retinal blood vessels and a very low blood flow value for papillary tissue blood flow, etc. is observed, it is most suitable as a place from which blood flow data used for personal authentication are extracted.

In order to guide this location to the observation field, in the case of the right eye the light-emitting diode 10 is turned on, and in the case of the left eye the light-emitting diode 9 is turned on. In the present invention, a mechanism for finely adjusting the direction of the line of sight is provided which employs a method in which the positions of these diodes are changed or a diode matrix, etc. is used and the position that is lit up is changed. This enables the location of the blood flow map to be freely selected, and registering a plurality of maps and sequentially switching between these maps can be utilized as a defense against impersonation.

Figure 5:
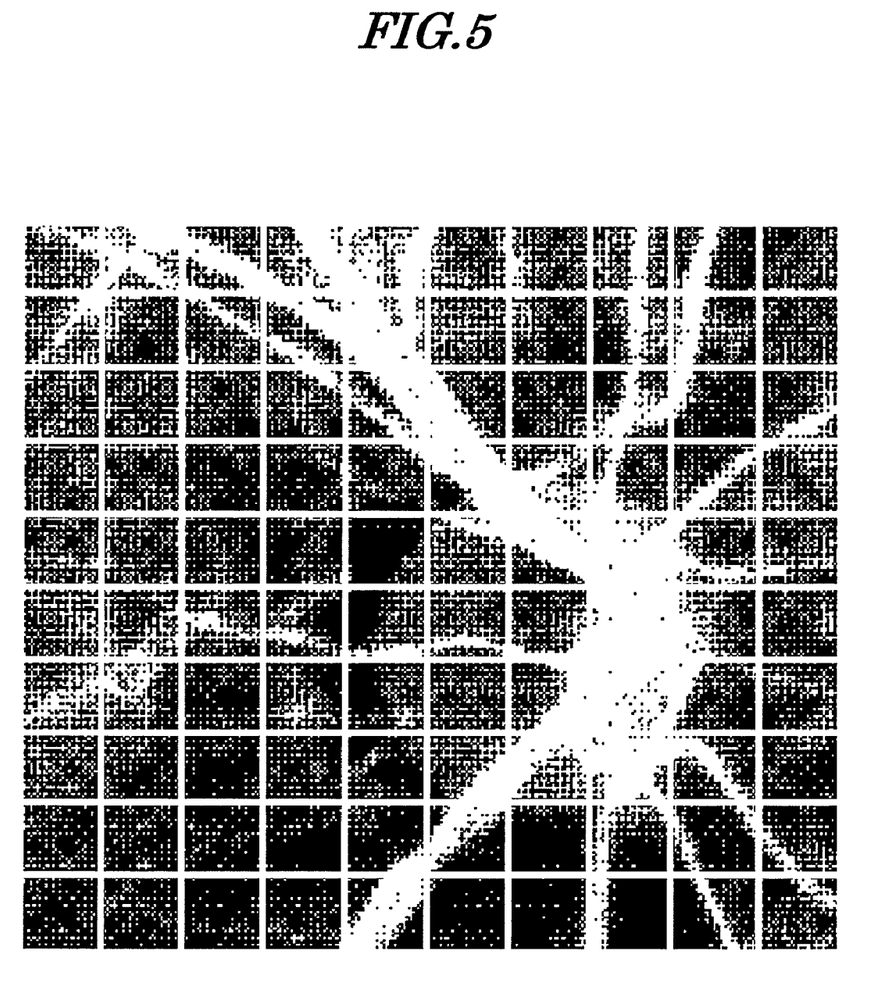
(FIG. 5) An example in which an ocular fundus blood flow map is divided into 10×10 zones.

In the invention of Claim 1, authentication may be carried out by, for example, dividing the blood flow map of FIG. 2 into 10×10=100 zones as shown in FIG. 5, reading in blood flow values of each region, and verifying them against a pre-registered distribution of values for each region of an individual.

Alternatively, authentication may be carried out by reading in blood flow values for each region of the 100 zones, examining the manner in which the value increases and decreases due to the pulse, and carrying out verification thereof against a pre-registered degree to which the value of an individual increases and decreases in each region, the gradient of the rise and fall, etc.

Furthermore, if the average blood flow values for 100 zones in FIG. 5 are determined and the numerical values are ranked, the sequence can be appended with, for example, (7,2), (4,6), etc., and this can be utilized as one set of authentication data. This is an advantage of the present invention due to an analog quantity, that is, blood flow distribution, being used. Furthermore, since this sequence changes when the laser wavelength is changed, a synergistic effect obtained by comparing each sequence with a registered sequence can improve the authentication accuracy.

Alternatively, when a blood vessel extends over several zones, the average blood flow value, the degree to which the value increases and decreases due to the pulse, the timing of change, etc. have close values for adjacent zones. By examining the degree of correlation between a given zone and its adjacent zones in terms of the above values, and checking against preregistered information of the subject, this also can be utilized as authentication data.

In the present invention, light emitted, for example, from a small laser light source such as a semiconductor laser is expanded through an optical system, and made to irradiate a wide area of the ocular fundus. This irradiated spot is imaged on a light-receiving face of a CCD camera, etc. through a lens. Image signals obtained from the CCD camera are A/D converted and taken into a personal computer or a microcomputer, and a quantity representing the rate of change with respect to time of the amount of light received for each pixel, for example, the average rate of change with respect to time, or the reciprocal of the magnitude of the variation in the amount of light received integrated over the exposure time of the image sensor is calculated, and displayed as a map as necessary, thus giving blood flow map data.

The blood flow distribution in blood vessels of the retina or a pattern of the course of blood vessels appear in the thus-obtained map of ocular fundus blood flow. On the other hand, laser light that has reached the choroid, which is a layer below the retina, strikes the choroid blood vessel layer and, observed so as to be superimposed on the blood flow map of the retinal blood vessels, which are fine and sharp, gives another map with low blood flow values that is faint overall and has a blurred outline.

In accordance with the present invention, there is provided a device for carrying out a personal authentication method comprising the above-mentioned steps. The device of the present invention is a personal authentication device comprising one or a plurality of, preferably two, irradiating means that expand a laser beam and irradiate the ocular fundus, light-receiving means that has a large number of pixels and receives light reflected from the ocular fundus, storage means that stores the output of each pixel obtained by the light-receiving means, calculating means that calculates a quantity representing the rate of change with respect to time of the amount of light received for each of the pixels using the stored contents of the storage means, second storage means that stores a two-dimensional distribution of the calculation results obtained for each of the pixels as a blood flow map, and means for comparing and evaluating the blood flow map stored by the second storage means against pre-registered personal data. When a near-infrared laser beam and a visible laser beam carry out irradiation at the same time, it is necessary to employ two or more irradiation means, but when they carry out irradiation in sequence or when only a near-infrared laser beam carries out irradiation, only one irradiation means is required.

As irradiation means, for example, light emitted from a semiconductor laser is expanded through a lens, and made to irradiate a wide region of the ocular fundus all at once. As light receiving means, an image sensor such as a line sensor or an area sensor is used. Electrical signals from the sensor are A/D converted and then stored in a storage section of a microcomputer or a personal computer. Image signals are taken into the storage section continuously over a few seconds, the difference between two consecutive images is determined using a pre-set program in the microcomputer or the personal computer, and the rate of change with respect to time of the amount of light received is calculated. Alternatively, the rate of change with respect to time of the amount of light received is calculated by utilizing the blur rate of an image, that is, the property that, when the light intensity changes at high speed within the exposure time of an image sensor, signals are integrated, and the difference between the two images decreases. The calculation results may be displayed as a two-dimensional color map on a personal computer screen in accordance with the position of each pixel. Means for comparing and evaluating the values thus calculated or a blood flow map displayed on display means against a pre-registered blood flow map of an individual may employ various types of conventionally known means.

The method and the device of the present invention may also employ a method/means for measuring a change in blood flow variation with respect to time, determining the slope of the rise and the slope of the fall of a waveform, detecting that the slope is steep on rising and gentle on falling, and determining that the subject is living.

EXAMPLES

In FIG. 1, 1 denotes an eyeball, 2 denotes a pupil, 3 denotes a spot of a laser beam passing through the pupil, 4 denotes a target location for imaging blood flow at a laser spot on the ocular fundus, 5 denotes a semiconductor laser, 6 denotes a mirror, 7 denotes a lens for projecting the laser on the ocular fundus, 8 denotes an objective lens for imaging the ocular fundus on an imaging system, 9 and 10 are light-emitting diodes for guiding the line of sight, 11 denotes a dichroic mirror, 12 denotes an optical system for observing the pupil and its surroundings, and 13 and 14 are image sensors such as a CCD camera. The area inside broken line 15 denotes the overall sensor section of the present invention.

A laser beam emitted from the semiconductor laser 5 is brought to a focus inside the pupil by the lens 7, and reducing the spot size when passing through the pupil makes the beam resistant to being vignetted by the pupil and enlarges the spot projected on the retina. An image of the laser spot on the ocular fundus is formed on the image sensor 14 via the objective lens 8 and the dichroic mirror 11, which allows only the laser wavelength to pass through. In this process, a speckle field reflecting a blood flow rate distribution in the retina is formed on the image plane, and analyzing this by computer enables a retinal blood flow map, as shown in FIG. 2, to be extracted.

INDUSTRIAL APPLICABILITY

The personal authentication system in accordance with the present invention combines a complex ocular fundus blood flow distribution with information on the change thereof over time, and forgery is therefore difficult. Utilizing this advantage enables its utilization in immigration control, room entrance/exit surveillance where a high degree of security control is required, etc.

What is claimed is:

1. A personal authentication method comprising imaging, on an image sensor as a laser speckle using an optical system, light reflected from retinal blood vessels of the ocular fundus and a blood vessel layer in ocular fundus internal tissue when a laser beam is expanded and made to irradiate the ocular fundus, calculating a quantity that represents the rate of change with respect to time of the amount of light received for each pixel of the laser speckle, obtaining an ocular fundus blood flow map as a two-dimensional map of numerical values of the quantity, and comparison-checking the blood flow map against pre-registered personal data, wherein the blood flow map obtained from reflected light is measured using a laser beam that can reach the internal tissue of the ocular fundus, and comparison-checking against pre-registered personal data is carried out utilizing at least one, observed in the blood flow map, of blood flow distribution data, a pattern reflecting the course of retinal blood vessels, a pattern reflecting the course of blood vessels in ocular fundus internal tissue observed superimposed thereon, and data on change thereof over time.

2. The personal authentication method according to claim 1, wherein as the laser beam one or a plurality of laser beams in the range of visible light to near-infrared light is used.

3. The personal authentication method according to claim 2, wherein light from the laser beam is near-infrared laser light having the wavelength in the range of about 770 to 1500 nm.

4. The personal authentication method according to claim 2, wherein a camera section that can observe a position of the laser beam when passing through the pupil is provided separately, and positioning of the optical system is controlled by processing an image signal obtained from the camera section.

5. The personal authentication method according to claim 2, wherein in order to observe the course of blood vessels in the optic papilla region the line of sight is guided.

6. The personal authentication method according to claim 1, wherein light from the laser beam is near-infrared laser light having the wavelength in the range of about 770 to 1500 nm.

7. The personal authentication method according to claim 6, wherein a camera section that can observe a position of the laser beam when passing through the pupil is provided separately, and positioning of the optical system is controlled by processing an image signal obtained from the camera section.

8. The personal authentication method according to claim 6, wherein in order to observe the course of blood vessels in the optic papilla region the line of sight is guided.

9. The personal authentication method according to claim 1, wherein a camera section that can observe a position of the laser beam when passing through the pupil is provided separately, and positioning of the optical system is controlled by processing an image signal obtained from the camera section.

10. The personal authentication method according to claim 9, wherein in order to observe the course of blood vessels in the optic papilla region the line of sight is guided.

11. The personal authentication method according to claim 1, wherein in order to observe the course of blood vessels in the optic papilla region the line of sight is guided.

12. A personal authentication device comprising one or a plurality of irradiating means that expand a near-infrared laser beam and irradiate the ocular fundus, light-receiving means that has a large number of pixels and receives light reflected from retinal blood vessels of the ocular fundus and a blood vessel layer in ocular fundus internal tissue, storage means that stores the output of each of the pixels obtained by the light-receiving means, calculating means that calculates a quantity representing the rate of change with respect to time of the amount of light received for each pixel using stored contents of the storage means, second storage means that stores a two-dimensional distribution of the calculation results obtained for each of the pixels as a blood flow map, means for extracting at least one, observed in the blood flow map stored by the second storage means, of blood flow distribution data, a pattern reflecting the course of retinal blood vessels, a pattern, observed superimposed thereon, reflecting the course of blood vessels in ocular fundus internal tissue, and data on changes thereof over time, and means for comparing and judging the extracted data against pre-registered personal data.

13. The personal authentication device according to claim 12, wherein a camera section that can observe the position of the laser beam when passing through the pupil is provided separately, and the device comprises means for controlling the positioning of the optical system by processing an image signal obtained from the camera section.

14. The personal authentication device according to claim 13, wherein the device comprises means for guiding the line of sight in order to observe the course of blood vessels in the optic papilla region.

15. The personal authentication device according to claim 12, wherein the device comprises means for guiding the line of sight in order to observe the course of blood vessels in the optic papilla region.

* * * * *